US00PP35544P2

(12) United States Plant Patent
Van Swieten

(10) Patent No.: US PP35,544 P2
(45) Date of Patent: Dec. 12, 2023

(54) ***PHALAENOPSIS* ORCHID PLANT NAMED 'PHA988874'**

(50) Latin Name: ***Phalaenopsis* hybrid**
Varietal Denomination: PHA988874

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 18/445,194

(22) Filed: May 18, 2023

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHA988874', particularly characterized by having numerous attractive, white, flecked flowers with white and reddish-purple lips, flowers that are concave in lateral view, and apical lobe of the lip is striped and netted, is disclosed.

3 Drawing Sheets

Genus and species: *Phalaenopsis* hybrid.
Variety denomination: 'PHA988874'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA988874'.

The new *Phalaenopsis* plant is a product of a planned breeding program conducted by the inventor in Bleiswijk, the Netherlands. The objective of this breeding program was to create a new *Phalaenopsis* plant with numerous attractive white, flecked flowers with white and reddish-purple lips suitable for potted plant production.

The new *Phalaenopsis* plant 'PHA988874' is a result of cross-pollination made by the inventor in October 2015 in Bleiswijk, the Netherlands, of the proprietary female, or seed parent, *Phalaenopsis* hybrid '6240-02' (unpatented), with a proprietary male, or pollen parent, *Phalaenopsis* hybrid '35069-01' (unpatented).

The new *Phalaenopsis* was selected by the inventor as a single plant within the progeny of the stated cross-pollination in a controlled greenhouse in Bleiswijk, the Netherlands, in July 2018. Asexual reproduction of the new *Phalaenopsis* plant by meristem tissue culture since 2019 in Bleiswijk, the Netherlands, has demonstrated that the new variety reproduces true to type with all of the characteristics, as herein described, firmly fixed and retained through successive generations.

Community Plant Variety Rights for this variety have not been applied for in the European Union. 'PHA988874' has not been made publicly available or sold anywhere in the world prior to the effective filing date of this application with the exception of sales or disclosures made one year or less before the effective filing date of this claimed invention by Applicant who obtained 'PHA988874' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA988874' as a new and distinct variety of *Phalaenopsis* plant:

1) white, flecked flowers with white and reddish-purple lip (number and intensity of flecks depend on the temperature during growing period);
2) flower shape in lateral view is concave; and
3) apical lobe of the lip is striped and netted.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in February 2023. Colors in the photographs may differ from the color values cited in the detailed botanical description, which accurately describe the actual colors of the new variety.

DESCRIPTION OF THE NEW VARIETY

Figure 1:
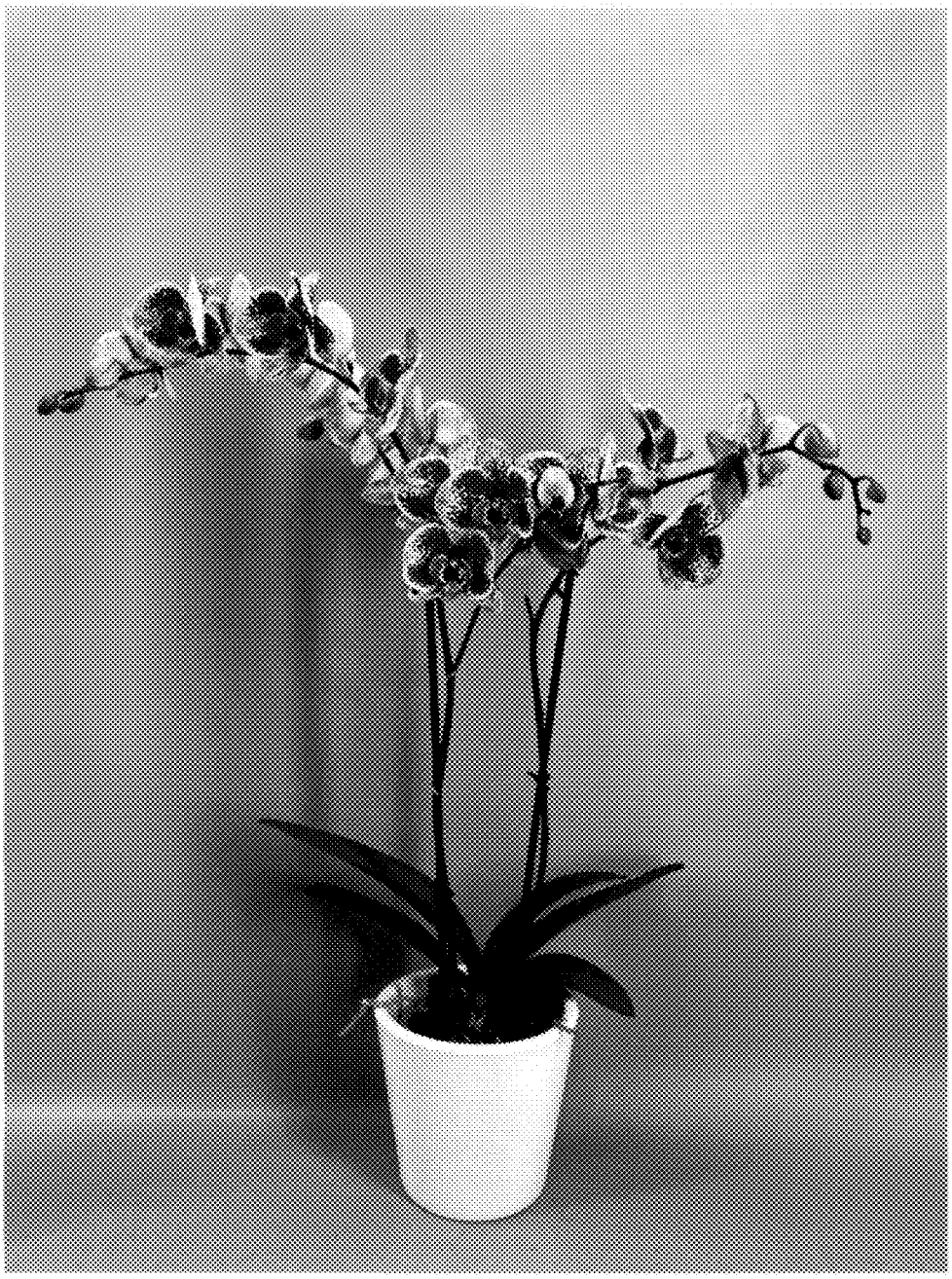
FIG. 1 shows the overall plant habit, including blooms, buds, and foliage of 'PHA988874'.
Figure 2:
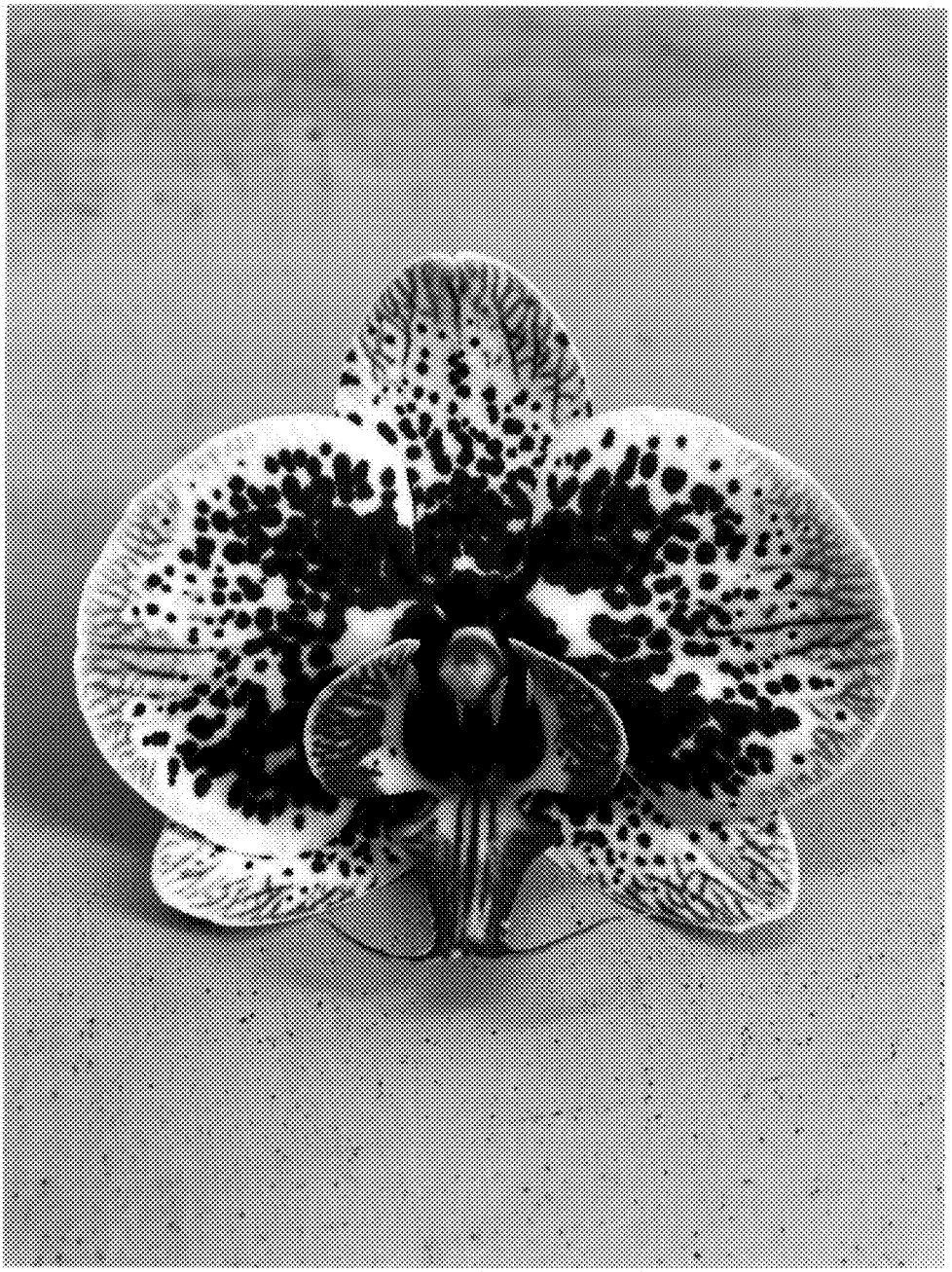
FIG. 2 shows a close-up of a flower of 'PHA988874'.
Figure 3:
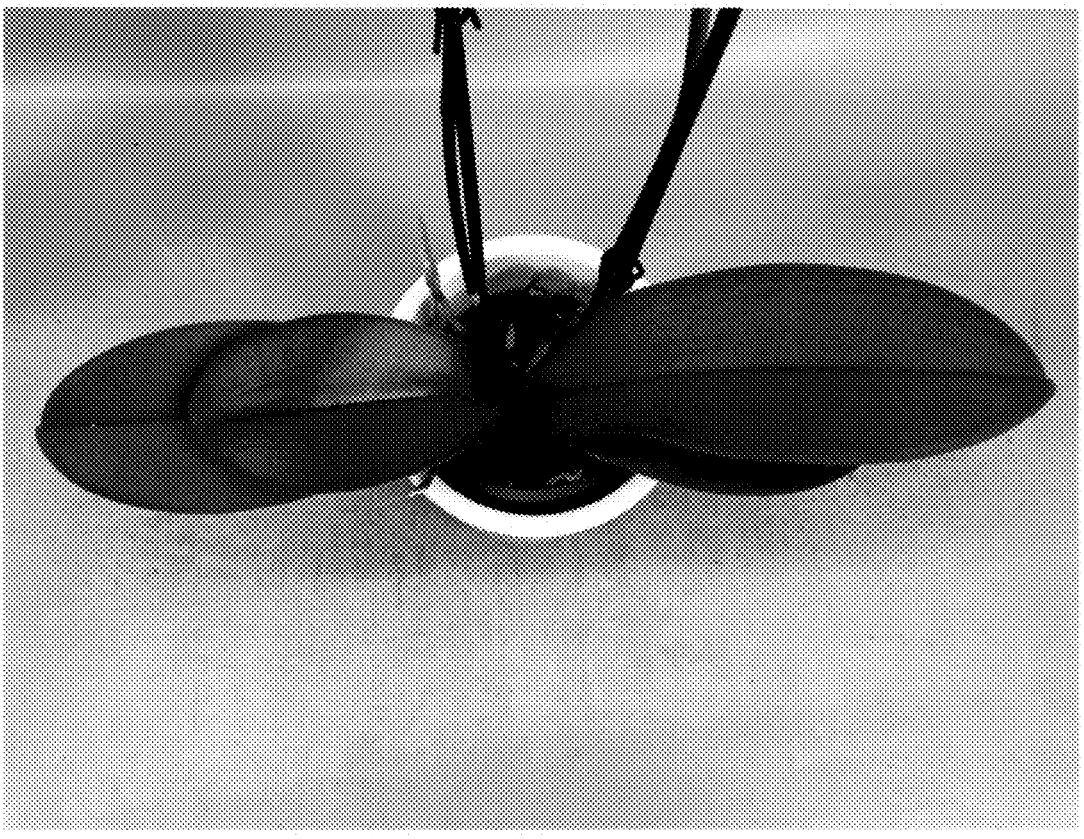
FIG. 3 shows a close-up, overhead view of the leaves of 'PHA988874'.

The following detailed description sets forth the distinctive characteristics of 'PHA988874'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in February 2023 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA988874'.

Parentage:

*Female parent*.—*Phalaenopsis* cultivar '6240-02' (unpatented).

*Male parent*.—*Phalaenopsis* cultivar '35069-01' (unpatented).

Propagation:

*Type*.—Meristem tissue culture.

Roots:

*Root description*.—Greyed-green (a color in between RHS 190B and RHS 190C) colored roots with branching lateral roots having light yellow-green (RHS 145B) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 53.0 cm to 63.0 cm.

*Width* (*measured from leaf tips*).—About 31.0 cm to 33.0 cm.

*Vigor*.—Strong.

Leaves:

*Mature leaves*.—Quantity per plant: 6 to 8 leaves are produced before flowering. Length (fully expanded): 16.0 cm to 19.0 cm. Width: 7.0 cm to 8.0 cm. Position of the broadest part of the leaf: At the middle. Shape: Oblong. Base shape: Moderately elongated. Apex: Obtuse asymmetric. Leaf blade angle with the petiole (measured from the horizontal position): Between 20 degrees and 40 degrees. Leaf margin: Entire. Color: Upper surface: RHS 146A. Lower surface: RHS 146B. Texture (both upper and lower surfaces): Smooth. Thickness: 2.0 mm to 3.0 mm. Variegation: Absent. Venation: Pattern: Parallel. Color of the midvein: Upper surface: RHS 146A. Lower surface: RHS 146B.

Peduncle:

*Quantity per plant*.—2.

*Number of flowers per peduncle*.—10 to 20.

*Length*.—53.0 cm to 63.0 cm.

*Diameter*.—5.0 mm to 6.0 mm.

*Strength*.—Strong.

*Aspect*.—Upright to slightly pendent.

*Texture*.—Smooth.

*Color*.—Green (RHS 146B) with a touch of brown (RHS 200A).

*Internode length*.—3.0 cm to 4.0 cm.

Inflorescence description:

*Appearance*.—Upright to slightly pendent, panicle inflorescence with bilaterally symmetrical flowers that open in succession beginning with the lowermost flower.

*Number of inflorescences*.—2.

*Inflorescence size*.—Height (from base to tip): 280.0 mm to 380.0 mm.

*Flowering time*.—First flowers can be expected 10 to 11 months after planting in a 12-cm pot.

*Flower*.—Height: 70.0 mm to 75.0 mm. Diameter: 80.0 mm to 85.0 mm. Depth of lip: 20.0 mm to 22.0 mm.

*Flower shape*.—Concave.

*Flower longevity*.—On the plant: 12 to 14 weeks.

*Fragrance*.—Absent.

*Flower bud*.—Average size: Medium to large. Length: 28.0 mm to 30.0 mm. Width: 18.0 mm to 20.0 mm. Shape: Egg shaped. Color: Light yellow-green (RHS 145D) with diluting flecks RHS N77C; a touch of reddish-purple (RHS N78B) on margins of sepals and toward the tip.

*Petals*.—Arrangement: Open/free. Shape: Semi-circular. Apex: Emarginated asymmetric. Margin: Weakly undulated. Length (from base to tip): 37.0 mm to 39.0 mm. Width: 43.0 mm to 45.0 mm. Position of the broadest part of the petal: Toward the base. Color (when fully opened): Upper surface: Basic color: White (RHS NN155C). Over color: Dark purple-red flecks (a color in between RHS N78A and RHS N79C); reddish-purple midvein (RHS N78B) and purplish-red netting (RHS N78C) toward apex. Lower surface: Basic color: White (RHS NN155C). Over color: Reddish-purple fading flecks (RHS N79D) and purplish-pink netting (RHS N78C). Number of spots and stripes on the petals (upper surface): Many flecks and very few stripes. Color of spots and stripes on the petals (upper surface): Flecks, a color in between RHS N78A and RHS N79C, and stripes RHS N78B. Density of netting of the petals (upper surface): Medium. Color of the netting (upper surface): RHS N78C.

*Dorsal sepal*.—Shape: Elliptic. Apex: Slightly emarginated symmetric. Margin: Entire. Length (from base to tip): 38.0 mm to 40.0 mm. Width: 26.0 mm to 28.0 mm. Position of the broadest part of the dorsal sepal: At middle. Color (when fully opened): Upper surface: Basic color: White (RHS NN155C). Over color: Dark purple-red flecks (a color in between RHS N78A and RHS N79C) and purplish-red netting (RHS N78C) toward apex. Lower surface: Basic color: White (RHS NN155C). Over color: A touch of light yellow-green (RHS 145D) at the base; light reddish-purple (RHS N78D) toward tip and diluting flecks RHS N79D. Number of spots and stripes on the dorsal sepal (upper surface): Many flecks. Color of spots and stripes on the dorsal sepal (upper surface): A color in between RHS N78A and RHS N79C. Density of netting of the dorsal sepal (upper surface): Medium. Color of the netting (upper surface): RHS N78C.

*Lateral sepals*.—Shape: Ovate. Apex: Obtuse asymmetric. Margin: Weakly undulated. Length (from base to tip): 41.0 mm to 43.0 mm. Width: 23.0 mm to 25.0 mm. Position of the broadest part of the lateral sepals: Toward the base. Color (when fully opened): Upper surface: Basic color: White (RHS NN155C). Over color: Dark purple-red flecks (a color in between RHS N78A and RHS N79C) and reddish-purple netting (RHS N78B) toward apex. Lower surface: Basic color: White (RHS NN155C). Over color: Light yellow-green (RHS 145D) at the base toward center; fading reddish-purple flecks (RHS N79D) and light reddish-purple (RHS N78D) toward margin on one side; reddish-purple midvein (RHS N78B) toward the tip. Number of spots and stripes on the lateral sepals (upper surface): Many flecks. Color of spots and stripes on the lateral sepals (upper surface): A color in between RHS N78A and RHS N79C. Density of netting of the lateral sepals (upper surface): Medium. Color of the netting (upper surface): RHS N78B.

*Labellum* (*lip*).—Whiskers: Present. Length of whiskers: 13.0 mm to 15.0 mm. Color of whiskers: Reddish-purple (RHS N78A) with white margins and tips (RHS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Moderately undulated. Length: 20.0 mm to 22.0 mm. Width: 14.0 mm to 16.0 mm. Color: Upper surface: Dark red-purple fleck (a color in between RHS 187B and RHS N79C) at the base, and a touch of light greenish-yellow (RHS 4C) on one side; white (RHS NN155C), very light purple (RHS 76B) with reddish-purple stripes and netting (RHS N78A) toward one margin and the tip. Lower surface: White (RHS NN155C); very light purple (RHS 76C) and diluting reddish-purple stripes (RHS N78B) toward the tip. Number of spots and stripes on the lateral lobe: One fleck and medium stripes. Color of spots and stripes on the lateral lobe: Fleck, a color in between RHS 187B and RHS N79C, and stripes RHS N78A. Density of netting of the lateral lobe: Medium. Color of the netting: RHS N78A.

*Apical lobe*.—Shape: Triangular. Margin: Entire. Length: 19.0 mm to 21.0 mm. Width: 18.0 mm to 20.0 mm. Color: Upper surface: White (RHS NN155C) with a touch of very light greenish-yellow (RHS 8C) at the base; dark purplish-red midvein (RHS N79C), light reddish-purple (RHS N78D) with reddish-purple stripes (RHS N78B) and netting (RHS N78A) toward margins and whiskers. Lower surface: White (RHS NN155C); reddish-purple stripes (RHS N78B) from the base, reddish-purple netting (RHS N78A) toward wings and margins. Number of spots and stripes on the apical lobe: Few stripes. Color of spots and stripes on the apical lobe: RHS N78B. Density of netting of the apical lobe: Low. Color of the netting: RHS N78A. Bump and ridge (upper and lower surface): Absent.

*Callus*.—Average size: Medium. Height: 6.0 mm to 7.0 mm. Length: 4.0 mm to 5.0 mm. Width: 4.0 mm to 5.0 mm. Color: Greenish-yellow (RHS 6C) front side; white (RHS NN155C) on sides; dark red (RHS 187A) toward tips.

Reproductive organs:

*Column*.—Length: 8.0 mm to 9.0 mm. Diameter: 5.0 mm to 6.0 mm. Color: White (RHS NN155C) at the base; reddish-purple (RHS N78B) toward the tips.

*Pollinia*.—Quantity: 2. Diameter: 1.0 mm to 1.2 mm. Color: Orange (RHS 24A).

*Ovary*.—Length: 11.0 mm to 13.0 mm. Diameter: 2.4 mm to 2.6 mm.

*Pedicel*.—Length: 35.0 mm to 37.0 mm. Diameter: 2.7 mm to 3.0 mm. Color: A touch of dark purplish-red (RHS N79A) at the base; light yellow-green (RHS 145C) with a touch of light purple (RHS 76A) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA988874' differs from the female parent plant, cultivar '6240-02' (unpatented), in that 'PHA988874' has white petals having many flecks and a dark red callus, whereas '6240-02' has reddish-purple petals with no flecks and a yellow callus.

'PHA988874' differs from the male parent plant, cultivar '35069-01' (unpatented), in that 'PHA988874' has panicle inflorescence, emarginated petals, and more narrow flowers whereas '35069-01' has raceme inflorescence, rounded petals, and wider flowers.

'PHA988874' is most similar to the commercial *Phalaenopsis* plants named 'PHALGULFQ' (U.S. Plant Pat. No. 29,975) and 'PHA632612' (U.S. application Ser. No. 17/803,999). 'PHA988874' differs from the commercial variety 'PHALGULFQ' in that 'PHA988874' has reddish-purple whiskers with white margins and tips, apical lobe is striped and netted, and medium curvature of the lateral lobes, whereas 'PHALGULFQ' has very light purple whiskers, shaded apical lobe, and weak curvature of lateral lobes. Additionally, 'PHA988874' has longer whiskers than 'PHALGULFQ'.

'PHA988874' differs from the commercial variety 'PHA632612' in that 'PHA988874' has white petals, reddish-purple whiskers with white margins and tips, and a striped and netted apical lobe, whereas 'PHA632612' has light reddish-purple petals, purple-red whiskers with yellow tips, and even pattern of apical lobe. Additionally, 'PHA632612' has longer whiskers than 'PHA988874'.

I claim:

1. A new and distinct variety of *Phalaenopsis* plant named 'PHA988874', substantially as described and illustrated herein.

* * * * *